United States Patent
Law et al.

(10) Patent No.: US 7,060,177 B2
(45) Date of Patent: Jun. 13, 2006

(54) METHOD AND APPARATUS FOR MEASURING ELECTROCHEMICAL CORROSION POTENTIAL INSIDE SMALL SHALLOW CRACKS

(75) Inventors: Robert James Law, Livermore, CA (US); David Phillip Siegwarth, San Jose, CA (US)

(73) Assignee: General Electric Company, Schenectady, NY (US)

( * ) Notice: Subject to any disclaimer, the term of this patent is extended or adjusted under 35 U.S.C. 154(b) by 612 days.

(21) Appl. No.: 10/401,645

(22) Filed: Mar. 28, 2003

(65) Prior Publication Data

US 2004/0188274 A1 Sep. 30, 2004

(51) Int. Cl.
*G01N 27/403* (2006.01)

(52) U.S. Cl. .............. 205/775.5; 204/404; 204/409
(58) Field of Classification Search ............ 205/775.5; 204/404, 409, 416; 376/245
See application file for complete search history.

(56) References Cited

U.S. PATENT DOCUMENTS

| | | | | |
|---|---|---|---|---|
| 2,993,366 A | * | 7/1961 | Birkness | 73/86 |
| 3,627,493 A | * | 12/1971 | Manley | 422/53 |
| 5,465,278 A | | 11/1995 | Cowan, II et al. | |
| 6,391,173 B1 | | 5/2002 | Kim et al. | |
| 6,440,297 B1 | | 8/2002 | Kim et al. | |

* cited by examiner

*Primary Examiner*—Alex Noguerola
(74) *Attorney, Agent, or Firm*—Armstrong Teasdale LLP (57) ABSTRACT

A method of measuring an electrochemical corrosion potential (ECP) of a material specimen using a detecting device including an ECP detecting array is provided. The method includes locating an offset spacer in close contact to a face of the ECP detecting array, locating the material specimen within the detecting device with a measurement face in close contact to the offset spacer, establishing a flow through the detecting device, and measuring an electrical potential between the detecting device ground and an electrode wire.

20 Claims, 4 Drawing Sheets

METHOD AND APPARATUS FOR MEASURING ELECTROCHEMICAL CORROSION POTENTIAL INSIDE SMALL SHALLOW CRACKS

BACKGROUND OF THE INVENTION

This invention relates generally to inspection of nuclear reactors, and more particularly to measuring an electrochemical corrosion potential (ECP) of a material sample.

The reactor pressure vessel (RPV) of a boiling water reactor (BWR) has a generally cylindrical shape and is closed at both ends, for example, by a bottom head and a removable top head. A top guide typically is spaced above a core plate within the RPV. A core shroud, or shroud, typically surrounds the core and is supported by a shroud support structure. Particularly, the shroud has a generally cylindrical shape and surrounds both the core plate and the top guide. There is a space or annulus located between the cylindrical reactor pressure vessel and the cylindrically shaped shroud.

The radiation field in an operating boiling water reactor (BWR) generates strong oxidizing species, such as oxygen and hydrogen peroxide. The presence of such oxidizing species contribute to the intergranular stress corrosion cracking (IGSCC) of 304 stainless steel components within the reactor. IGSCC is known to be a major environment-related material performance problem within BWRs. Lowering concentrations of ionic impurities and oxidizing species in the reactor water may facilitate mitigation of IGSCC. The electrochemical corrosion potential (ECP) of stainless steels and other active metals is known to be controlled by dissolved oxygen, hydrogen, and hydrogen peroxide concentrations in the BWR water and the hydrodynamic flow conditions within the water path. In order to evaluate or predict materials performance (including IGSCC as a function of time), it is desirable to know the ECP value of the structural materials that are exposed to high temperature water within the reactor pressure vessel.

In moderate hydrogen water chemistry (HWC), hydrogen is added to the feed water of a BWR to facilitate mitigating IGSCC. A purpose of adding hydrogen is to reduce the concentrations of dissolved oxidants in the reactor water and thus lower the ECP to a value that is less than approximately −230 mV, measured against a standard hydrogen electrode (SHE), at which IGSCC susceptibility is reduced. Hydrogen levels in the reactor water are maintained in excess of the stoichiometric amount needed to react with either oxygen or hydrogen to form water. However, there are several side effects of the moderate HWC application, such as increased nitrogen-16 carry-over to the turbine and higher cobalt-60 deposition rates. Also, the critical ECP value that is needed to prevent IGSCC is difficult to achieve in highly oxidizing and/or high water flow regimes.

Noble metal chemical addition (NMCA) improves the catalytic properties of metal surfaces for the recombination of either hydrogen/oxygen or hydrogen peroxide/hydrogen to form water, NMCA allows low metal surface ECP values to be achieved at lower hydrogen addition rates. This catalysis reduces the oxygen concentration at the metal surface to approximately zero, thus causing the ECP to drop to its thermodynamic minimum of approximately −550 mV SHE in pure water at 288 degrees Celsius. To achieve a stoichiometric excess of hydrogen, feed water hydrogen addition is adjusted to achieve a hydrogen:oxygen molar ratio of greater than 2:1, or a hydrogen:oxygen weight ratio of greater than 1:8 in the reactor water. Injection of NMCA chemicals, directly into the reactor water deposits noble metals onto the surfaces of reactor components that are exposed to the reactor water. The surfaces of the reactor components are typically covered with an oxide outer layer. The noble metals are deposited onto the oxide layer, thus providing a catalytic site for both the hydrogen/oxygen and hydrogen/peroxide recombination reactions. The ECP value needed to ensure protection of components from IGSCC can then be achieved through the addition of smaller amounts of hydrogen, thus avoiding many of the negative side effects that are frequently encountered at higher hydrogen concentrations. Evaluating the effectiveness of noble metal deposited within existing cracks is beyond current technology.

BRIEF DESCRIPTION OF THE INVENTION

In one aspect, a method of measuring an electrochemical corrosion potential (ECP) of a material specimen using a detecting device including an ECP detecting array is described. The method includes locating an offset spacer in close contact to a face of the ECP detecting array, locating the material specimen within the detecting device with a measurement face in close contact to the offset spacer, establishing a flow through the detecting device, and measuring an electrical potential between the detecting device ground and an electrode wire.

In another aspect, an apparatus for measuring an electrochemical corrosion potential of a material specimen is described. The apparatus includes a holder including a first end and a second end, the second end removably coupled to a fluid outlet. The holder includes, a detector array including a body having a plurality of bores therethrough, the body including a detecting face and a second opposing face. The detector array is contained in the holder first end, and includes at least one electrode including a tip and a wire. The at least one electrode is positioned in a portion of the plurality of bores such that an electrode tip extends outwardly from the detecting face and the wire extends from the tip, though the bore and extends from the second face, the tip and wire held frictionally in place within the bore. A fluid inlet is coupled to the holder such that fluid entering the inlet flows through a portion of the plurality of bores from the second face to the detecting face.

In still another aspect, an apparatus for measuring an electrochemical corrosion potential of a material specimen is described. The apparatus includes a holder including a first end, a second end removably coupled to a fluid outlet, and a resilient member engaged between the fluid outlet and a compression spacer such that a longitudinal compressive force is imparted from the fluid outlet through the resilient member to a first face of the compression spacer. The resilient member, fluid outlet connector, and compression spacer are co-axially aligned. The holder includes a detector array including a body having a plurality of bores therethrough, the body including a detecting face and a second opposing face. The detector array body is contained in the holder first end. The detector array includes at least one platinum wire electrode including a tip, the tip includes an expanded portion, and a wire. The electrode is positioned in a portion of the plurality of bores such that an electrode tip extends outwardly from the detecting face and the wire extends from the tip, though the bore and extending from the second face, the tip and wire held frictionally in place within the bore, and a fluid inlet coupled to the holder such that fluid entering the inlet flows through a portion of the plurality of bores from the second face to the detecting face.

DETAILED DESCRIPTION OF THE INVENTION

A basic principle of NMCA is that noble metal on a component surface lowers a surface ECP with an addition of excess hydrogen, which in turn lowers a chemical potential driving force that can elevate chemical ion concentrations at a crack tip. The crack tip is where the crack is spreading into the material. This is true on the component surface and for a small, shallow crack mouth opening where oxidants (oxygen and peroxides) are reacted to substantially zero by the noble metal catalyst with excess hydrogen in the bulk water.

As the crack mouth opens, the bulk concentration oxidants can be forced into the crack by flow induced eddies (generated in cross flow geometries, where an orientation of the crack length is substantially perpendicular to flow) or expansion region flow (in parallel crack length orientation). If the flow can carry sufficient oxidant into the crack below a depth of deposited catalyst (the electrochemical mouth, ECM) there may be an internal ECP driving force, in a region beyond the catalyst penetration in the crack. This condition concentrates ions at the crack tip and generates a crack rate not detected by surface ECP measurements.

A crack simulating monitoring assembly collects noble metal within a simulated crack which varies in noble metal concentration with penetration depth. The below described ECP measurement device performs ECP measurements on simulated crack surfaces acquired with a crack deposition monitor to determine the depth of catalyst penetration.

A material specimen from the crack deposition monitor is placed in the ECP measurement device to determine the catalyst penetration depth. In an exemplary embodiment, flow through the measurement device is from a detector array end wherein the dissolved gases (hydrogen and oxygen) would not come in contact with a catalyst surface until just prior to the electrode tips. In another embodiment, flow through the measurement device is from a material specimen insertion end.

An array of electrodes can distinguish very small separations of ECP, in the range of approximately 0.005 inches to 0.050 inches. In an exemplary embodiment, such sensitivity is achieved using a small detector tip, close to a measurement surface. In another embodiment, part of such sensitivity is achieved mathematically by iteration and curve simulation using oversized areas.

In the exemplary embodiment, four detectors make up the array. In an alternative embodiment, the number of electrodes within the array is increased to facilitate improving the definition and accuracy by adding electrodes at additional radial distances and angles.

Figure 1:
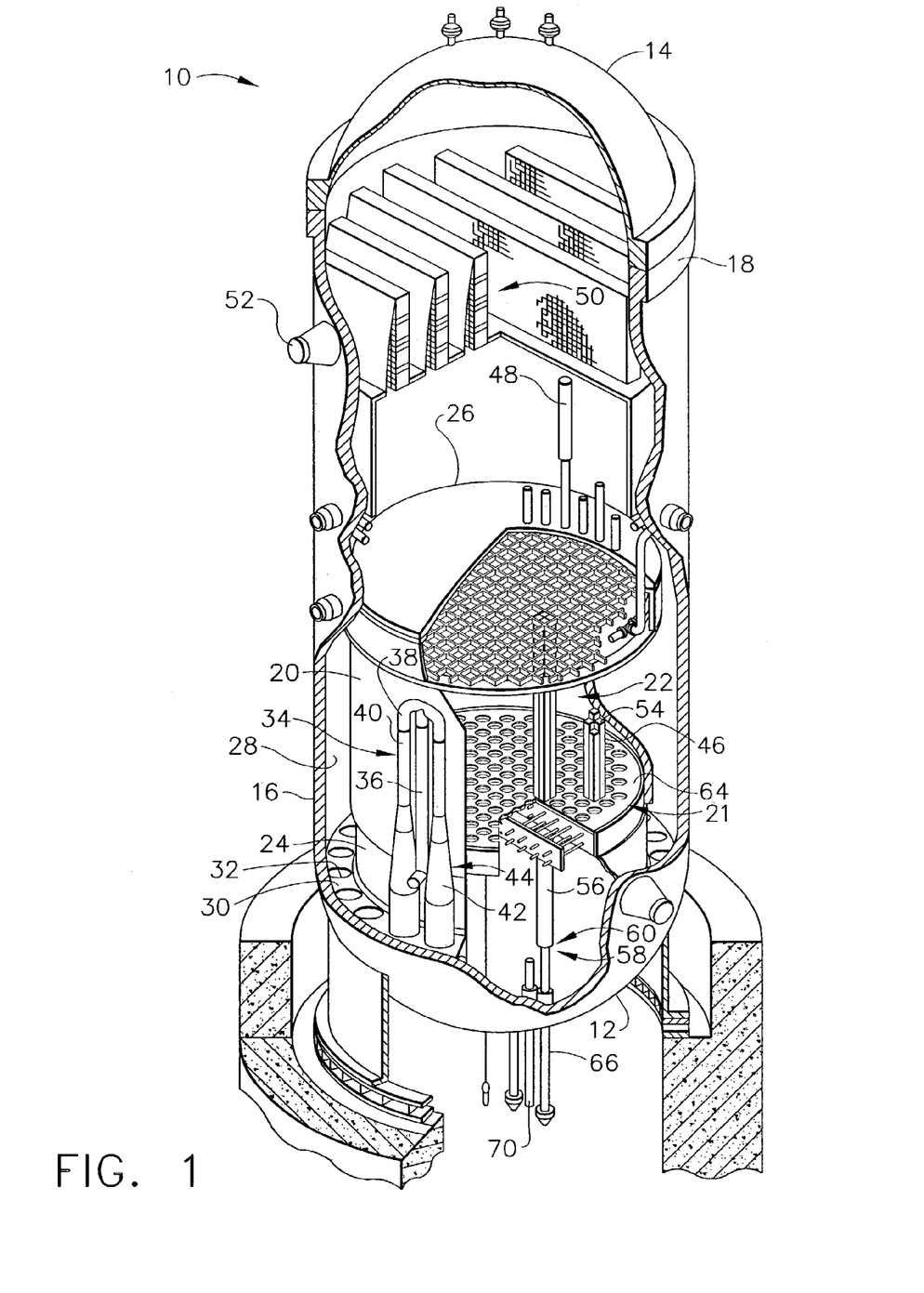
FIG. 1 is a sectional view, with parts cut away, of a boiling water nuclear reactor pressure vessel (RPV).

FIG. 1 is a sectional view, with parts cut away, of a boiling water nuclear reactor pressure vessel (RPV) 10. RPV 10 has a generally cylindrical shape and is closed at one end by a bottom head 12 and at its other end by a removable top head 14. A sidewall 16 extends from bottom head 12 to top head 14. Sidewall 16 includes a top flange 18. Top head 14 is attached to top flange 18. A cylindrically shaped core shroud 20 surrounds a reactor core 22 and a bypass water region, called a reflector 21. Core shroud 20 is supported at one end by a shroud support 24 and includes an opposed removable shroud head 26. A downcomer region 28 is an annulus formed between core shroud 20 and sidewall 16. A pump deck 30, which has a ring shape, extends between shroud support 24 and RPV sidewall 16. Pump deck 30 includes a plurality of circular openings 32, with each opening housing a jet pump 34. Jet pumps 34 are circumferentially distributed around core shroud 20. An inlet riser pipe 36 is coupled to two jet pumps 34 by a transition assembly 38. Each jet pump 34 includes an inlet mixer 40, and a diffuser 42. Inlet riser 36 and two connected jet pumps 34 form a jet pump assembly 44.

Heat is generated within core 22, which includes a plurality of fuel bundles 46 of fissionable material. Water circulated up through core 22 is at least partially converted to steam. A plurality of steam separators 48 separate steam from water, which is recirculated. A plurality of steam dryers 50 remove residual water from the steam. The steam exits the RPV 10 through a steam outlet 52 near vessel top head 14.

The amount of heat generated in core 22 is regulated by inserting and withdrawing a plurality of control rods 54 of neutron absorbing material, for example, hafnium. To the extent that control rod 54 is inserted adjacent fuel bundle 46, it absorbs neutrons that would otherwise be available to promote the chain reaction which generates heat in core 22.

Each control rod 54 couples through a control rod drive tube 56 with a control rod drive mechanism (CRDM) 58 to form a control rod apparatus 60. CRDM 58 moves control rod 54 relative to a core support plate 64 and adjacent fuel bundles 46. CRDM 58 extends through bottom head 12 and is enclosed in a control rod drive mechanism housing 66. A control rod guide tube 56 extends vertically from the control rod drive mechanism housing 66 to core support plate 64. Control rod guide tubes 56 restrict non-vertical motion of control rods 54 during control rod 54 insertion and withdrawal. Control rod guide tubes 56 can have any number of shapes, for example a cruciform shape, a cylindrical shape, a rectangular shape, a Y-shape, and any other suitable polygonal shape.

Figure 2:
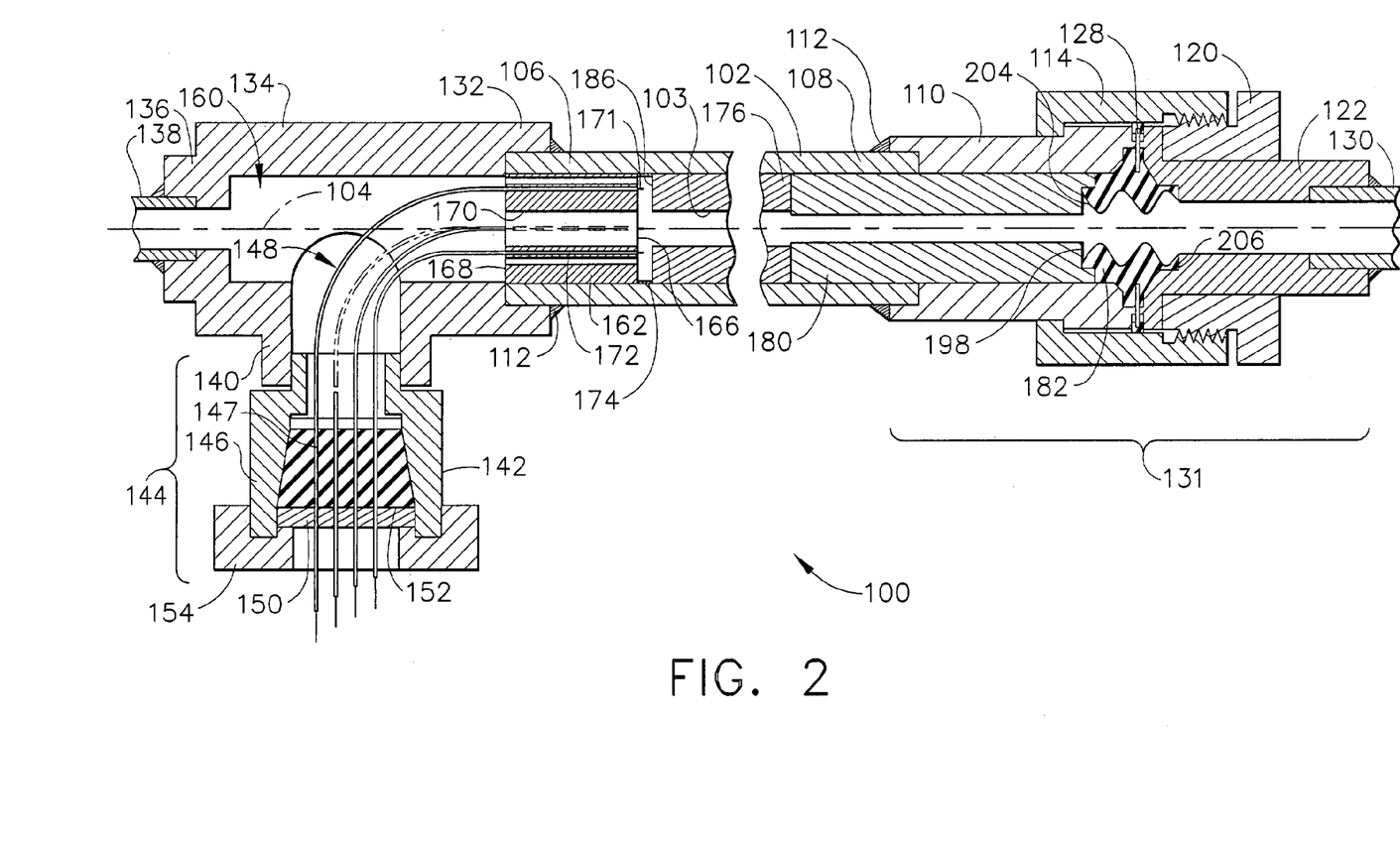
FIG. 2 is a cross-sectional view of an Electrochemical Corrosion Potential (ECP) measurement device.

FIG. 2 is a cross-sectional view of an Electrochemical Corrosion Potential (ECP) measurement device 100. Device 100 includes a cylindrical holder 102 with a specimen center bore 103 therethrough, a longitudinal axis 104, a holder inlet end 106, and a holder outlet end 108. A union inlet end 110 is coupled to holder outlet end 108, for example by a weld 112. In an alternative embodiment, union inlet end 110 is coupled to holder outlet end 108 by threads. Union inlet end 110 is coupled to a female nut 114. Female nut 114 is coupled to male nut 120, for example by threaded engagement. Male nut 120 includes a bore therethrough for receiving a union outlet end 122. When male nut 120 is threadily engaged to female nut 114 the union is sealed by a washer 128. The outlet end of union outlet end 122 is fixedly coupled to an outlet tubing 130, for example, by welding. Components union inlet end 110, union outlet end 122, washer 128, female nut 114, and male nut 120 make up a zero clearance union 131.

Holder inlet end 106 is fixedly coupled to a run 132 of a Tee 134. An alternate run 136 of Tee 134 is fixedly coupled to an inlet tubing 138. A branch 140 of Tee 134 is fixedly coupled to a body 142 of a gland seal fitting 144. Fitting 144 includes sealer 146 that includes at least one bore 147 therethrough for receiving a respective insulated electrical wire 148 therein. In one embodiment, wire 148 is a platinum wire approximately 0.020 inches in diameter. In an alternative embodiment, wire 148 is a metal oxide wire. Follower 150 couples to a first face 152 of sealer 146. Cap 154 threadily engages gland seal body 142 and engages follower 150. As cap 154 is turned to threadily engage gland seal body 142, cap 154 is drawn towards gland seal body 142. Since cap 154 is engaged to the face of follower 150, follower 150 is pushes on face 152 of sealer 146, as cap 154 is drawn towards gland seal body 142, sealer 146 is compressed, deforming to seal each bore 147. Sealer 146 collapses on wire 148, sealing bore 147 and facilitates creating a pressure tight barrier between an internal passage 160 of Tee 134 and ambient pressure.

A detector array 162 is retained inside holder 102 by Tee 134 shoulder on an inlet face 168 and offset spacer 174 on a detector face 166. Detector array 162 includes detector face 166, an opposing inlet face 168, at least one water bore (not shown in FIG. 2) and a central bore 170 therethrough. A distal end 171 of wires 148, which form an electrode tip 171, enter detector array 162 at a respective electrode bore 172, pass through electrode bore 172 and extend outwardly from detector face 166. Wires 148 are fixedly coupled to electrode bore 172. In one embodiment, wires 148 are pressed into electrode bore 172.

When fully assembled, device 100 also includes an offset spacer 174, a material specimen 176, a compression spacer 180, and a resilient member 182, such as a spring. In the exemplary embodiment, offset spacer 174 is a circular washer having a substantially planar body with an outside diameter such that offset spacer 174 fits slidily through the interior of holder 102. Offset spacer 174 has a predetermined thickness based on a distance electrode tips 171 extend from detector face 166. Offset spacer 174 is selected such that its width is greater than the distance electrode tips 171 extend outwardly from detector face 166. In the exemplary embodiment, offset spacer 174 is constructed of an electrically insulating material able to withstand temperatures greater than 288 degrees Celsius, such as, for example ceramic. A material specimen 176 includes a cylindrical body having a bore 103 therethrough, a measurement face 186 and a second face. An outside diameter of material specimen 176 is sized such that material specimen 176 is able to slide through the interior of holder 102. Measurement face 186 butts up to offset spacer 174. Compression spacer 180 includes a cylindrical body having a center bore therethrough and a recessed face 198. An outside diameter of compression spacer 180 is sized such that compression spacer 180 fits slidily through the interior of holder 102. Resilient member 182 is substantially cylindrically shaped. An outside diameter of resilient member 182 is sized such that resilient member 182 fits slidily against recessed face 198 and a shoulder 206 of union outlet end 122. Recessed face 198 and shoulder 206 align resilient member 182 coaxially with axis 104 and maintains a radial position of resilient member 182. Resilient member 182 is compressed by male nut 120 drawing closer to female nut 114 during a tightening process on male nut 120. In the exemplary embodiment, male nut 120 is threaded into female nut 114, the threading process drawing male nut 120 to female nut 114. In an alternative embodiment, a cam-lock device is used to engage male nut 120 and female nut 114 and draw them together. The compressive force generated by drawing male nut 120 to female nut 114 is transmitted through compression spacer 180 to material specimen 176. The compression force acting on material specimen 176 maintains a crack gap on measurement face 186 and maintains a consistent spacing between measurement face 186 and detector face 166.

In operation, measurement device 100 is loaded with material specimen 176 by first selecting a properly sized offset spacer 174. Offset spacer 174 is sized such that its thickness is greater than the distance electrode tips 171 extend outwardly from detector face 166. Offset spacer 174 is inserted into holder 102 and allowed to slide down to contact detector face 166 with offset spacer 174 coaxially aligned with axis 104. Material specimen 176 is inserted into holder 102 with measurement face 186 toward offset spacer 174. Compression spacer 180 is inserted into holder 102 with a planar face toward material specimen 176. Resilient member 182 is inserted into holder 102 such that a first face 204 of resilient member 182 butts up to recessed face 198. Union 131 is assembled to enclose removable components within holder 102 and seal an interior space of holder 102 from ambient pressure.

Electrode tips 171 are verified to not be grounded during the assembly process by measuring the resistance to ground of each electrode extension wire 148 and comparing a resistance value measured with a predetermined minimum allowable value. Flow is initiated through device 100 such that a temperature of fluid in device 100 is controlled to a range of about 250 degrees Celsius to about 310 degrees Celsius and a pressure of fluid in device 100 is controlled to a range of about 900 pounds per square inch gauge (psig) (6205 kilopascal (kPa)) to about 2200 psig (15,170 kPa). In another embodiment, a temperature of fluid in device 100 is controlled to a range of about 270 degrees Celsius to 300 degrees Celsius and a pressure of fluid in device 100 is controlled to a range of about 950 psig (6,550 kPa) to about 1200 psig (8274 kPa). In yet another embodiment, a temperature of fluid in device 100 is controlled to about 288 degrees Celsius and a pressure of fluid in device 100 is controlled to about 1000 psig (6895 kPa). Total flow through device 100 is determined by a pressure drop across device 100, a diameter of central bore 170, a number and diameter of water bores, and a thickness of offset spacer 174 used to separate electrode tips 171 from measurement face 186. In the exemplary embodiment, a concentration of dissolved hydrogen and oxygen is controlled to greater than about 2 molar ratio. In another embodiment, the concentration of dissolved hydrogen and oxygen is controlled to greater than about 1 molar ratio. When the above conditions are stable, an ECP measurement is taken between each electrode wire and holder 102, and recorded.

Figure 3:
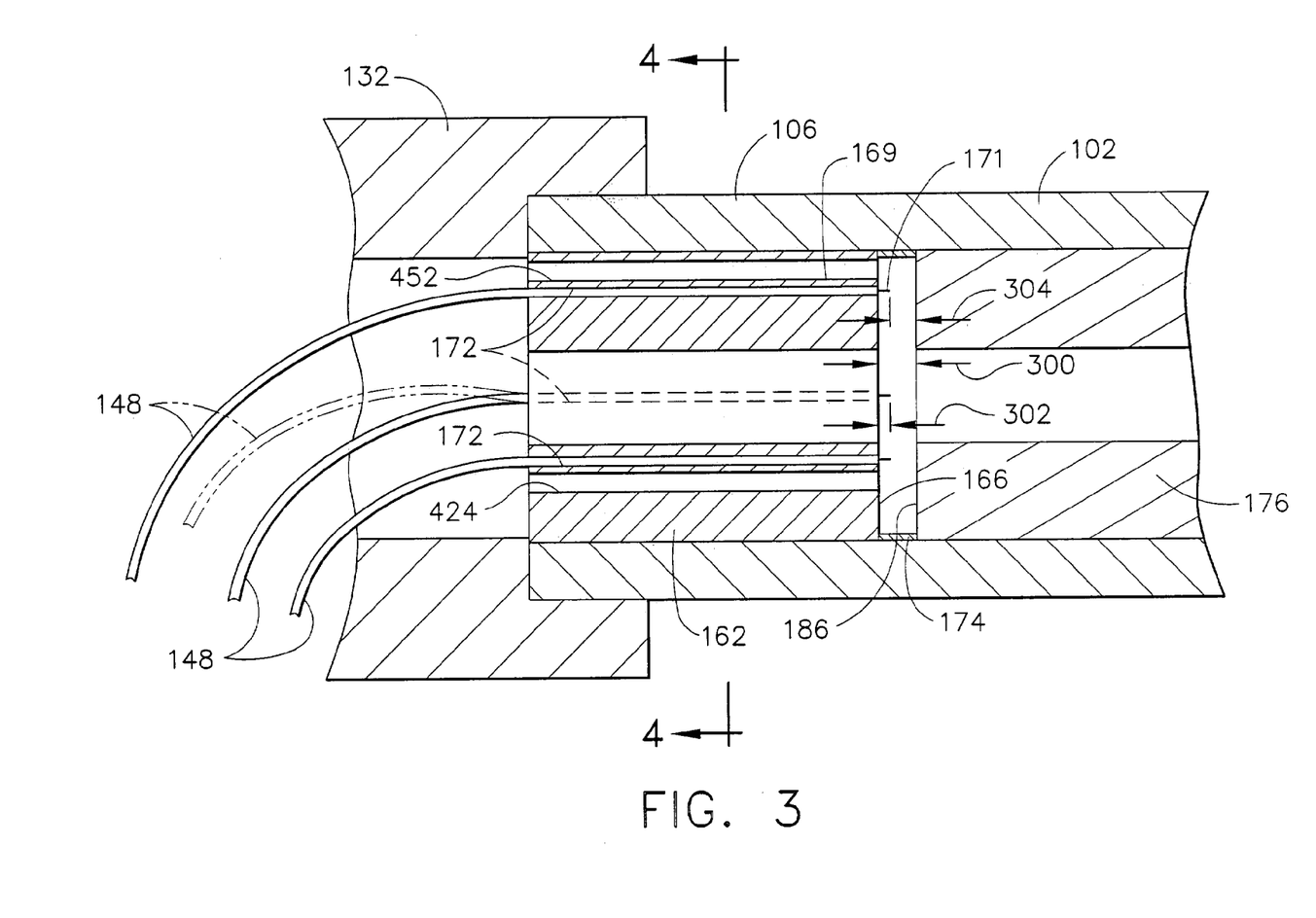
FIG. 3 is a close-up cross-sectional view of the ECP measurement device shown in FIG. 2.

FIG. 3 is a close-up cross-sectional view of measurement device 100 shown in FIG. 2. Detector array 162 is fixedly mounted at least partially within the inlet end 106 of holder 102. Electrode wires 148 are insulated platinum wires approximately 0.020 inches in diameter and are inserted into electrode bores 172 in detector array 162. A water bore 169 corresponding to each electrode bore 172 is formed outwardly radially from each respective electrode bore 172. In the exemplary embodiment, wires 148 are pressed into electrode bores 172 such that wires 148 are jammed into electrode bores 172 and become immovable during use of measurement device 100. In an alternative embodiment, wires 148 are crimped after insertion into electrode bores 172 such that a diameter of wires 148 expands proximate a location of crimping and facilitates holding wires 148 immovable in electrode bores 172 during use of measurement device 100. In another alternative embodiment, electrode bores 172 are at least partially tapered and configured to receive a corresponding expanded end of wires 148.

Electrode tips 171 are a distance 304 from measurement face 186. When distance 304 is made smaller by reducing the thickness of offset spacer 174, electrode tips 171 are sensitive to a smaller area on measurement face 186, therefore a measurement of ECP is more accurate than a measurement taken when distance 304 is larger.

A crevice width 300 is the distance between detector face 166 and measurement face 186. An electrode exposure distance 302 is the distance electrode tips 171 extend outwardly from detector face 166. Because there may be a plurality of electrodes used in detector array 162 and each electrode tip can extend outwardly from detector face 166 by a distance different than each other electrode tip 171, electrode exposure distance 302 is a distance the electrodes extends outwardly from detector face 166. Crevice width 300 is set by offset spacer 174, which is positioned between detector face 166 and measurement face 186 during assembly of device 100. A thickness of offset spacer 174 is selected such that crevice width 300 is greater than electrode exposure distance 302 yielding distance 304.

Figure 4:
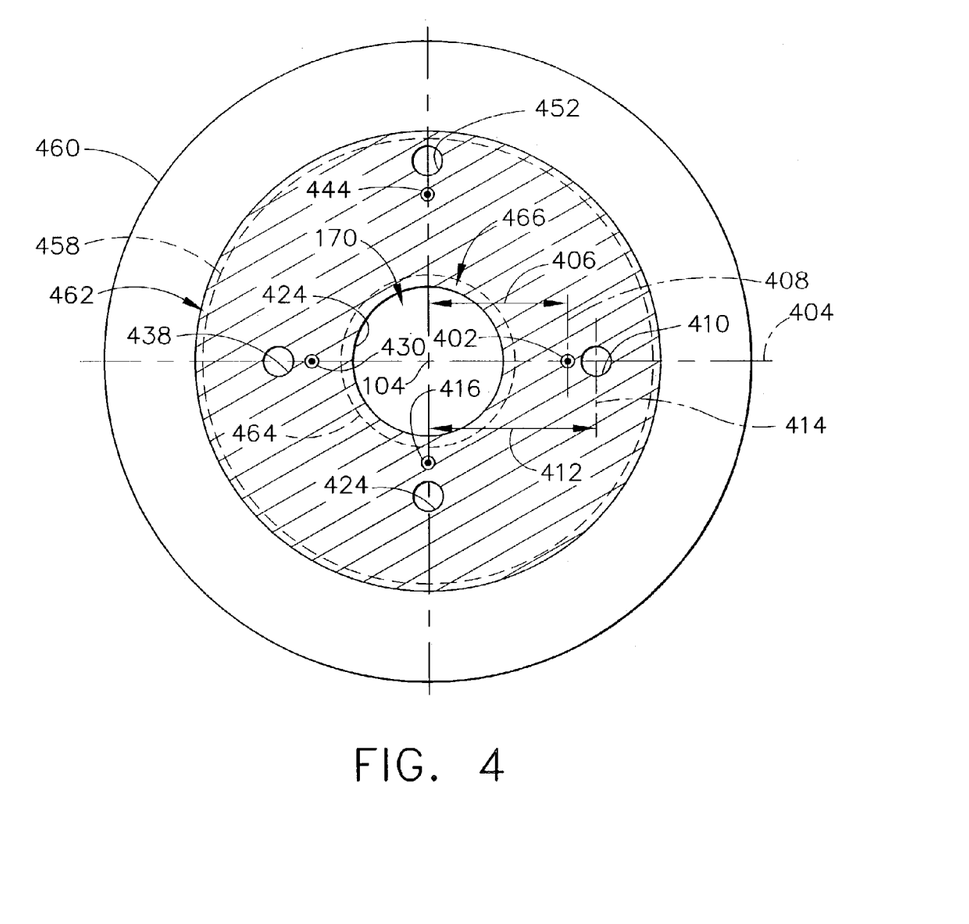
FIG. 4 is an end view of a detector array taken along an A—A section line as shown in FIG. 3.

FIG. 4 is an end view of detector array 162 taken along an A—A section line as shown in FIG. 3. A first electrode bore 402 is located on a radius 404 a distance 406 between a first electrode bore centerline 408 and longitudinal axis 104. A first water bore 410 is also located on a radius 404 a distance 412 between a first water bore centerline 414 and longitudinal axis 104. In the exemplary embodiment, electrode bores 416, 430, and 444 and respective water bores 424, 438, and 452 are shown at different radial distances, from longitudinal axis 104. The distance of electrode bore 416 from axis 104 is less than the distance of electrode 402 from axis 104, the distance of electrode bore 444 from axis 104 is less than the distance of electrode bore 416 from axis 104, and electrode bore 430 is closest to axis 104. The distance between each electrode bore and longitudinal axis 104 correlates to measuring an ECP for a different radial area on measurement face 186. In an alternative embodiment, the radial distances of the electrode bore positions around the array from axis 104 may be different.

In the exemplary embodiment, water bores 410, 424, 438 and 452 are shown directly outboard radially from electrode bores 402, 416, 430, and 444, respectively. In another embodiment, water bores 410, 424, 438 and 452 may be located differently such that water exiting water bores 410, 424, 438 and 452 flows past electrode bores 402, 416, 430, and 444 respectively, before contacting a catalyzed surface, or a surface on material specimen 176 that is not on measurement face 186. The water flowing past electrode bores 402, 416, 430, and 444 should be water that has not touched parts of material specimen 176 other than measurement face 186.

Edge 458 is an outer radial boundary of a measurable area on measurement face 186. Circular boundary 460 represents an outer peripheral boundary of detector array 162. An area 462 between edge 458 and boundary 460 is covered by offset spacer 174 when device 100 is fully assembled and therefore is unavailable for measurement. Inner peripheral edge 464 represents an inside diameter of material specimen 176. An area 466 is also unavailable for measurement.

In operation, fluid introduced into device 100 is distributed by a predetermined pressure drop into water bores 170, 410, 424, 438 and 452. Fluid exiting water bores 410, 424, 438 and 452 is forced to turn inward radially toward axis 104 due to measurement face 186 being crevice width 300 distance away from detector face 166 where the fluid is exiting water bores 410, 424, 438 and 452. As the fluid flows radially inward it passes over electrode bores 402, 416, 430, and 444 respectively, in which each contain an electrode tip 171. The fluid continues to flow radially inward until it joins fluid exiting central bore 170 where the fluid then exits device 100, first flowing through bore 103 and continuing to outlet tube 130.

The above-described ECP measurement device is cost-effective and highly reliable. The device includes a holder to position and secure a material specimen to be measured, a detector array to make the measurements and a flow system to provide a representative environment for the measurement. Such a device facilitates an assessment of the depth of noble metal penetration in cracks. As a result, the ECP measurement device facilitates improving reactor plant operation and maintenance in a cost-effective and reliable manner.

Exemplary embodiments of ECP measurement devices are described above in detail. The systems are not limited to the specific embodiments described herein, but rather, components of each device may be utilized independently and separately from other components described herein. The ECP measurement device components can also be used in combination with other ECP measurement device components.

While the invention has been described in terms of various specific embodiments, those skilled in the art will recognize that the invention can be practiced with modification within the spirit and scope of the claims.

What is claimed is:

1. A method of measuring an electrochemical corrosion potential (ECP) of a material specimen using a detecting device including an ECP detecting array, said method comprising:
    locating an offset spacer in close contact to a face of the ECP detecting array;
    locating the material specimen within the detecting device with a measurement face in close contact to the offset spacer;
    establishing a flow through the detecting device;
    measuring an electrical potential between the detecting device ground and an electrode wire.

2. The method in accordance with claim 1 wherein the detecting device includes an electrode including a tip, and wherein said locating an offset spacer further comprises:
    determining a distance an electrode tip extends beyond a measurement face of the detecting array; and
    selecting a spacer such that a thickness of the spacer is greater than the distance determined.

3. The method in accordance with claim 1 wherein the detecting device includes a compression spacer, and wherein said locating the specimen in the detecting device comprises:
    butting the specimen to the offset spacer such that the specimen measurement face contacts only a first face of the offset spacer and a second face of the offset spacer only contacts the detecting array;
    verifying the specimen is not in contact with an electrode tip of the detecting array; and
    locating the compression spacer within the detecting device wherein the compression spacer transmits a compressive force to the specimen.

4. The method in accordance with claim 3 wherein the detecting device includes a fluid outlet connector having a resilient member therein, and wherein said locating the specimen in the detecting device comprises:
    installing the fluid outlet connector such that the resilient member is in close contact to the compression spacer; and locking the fluid outlet connector to the detecting device such that the resilient member is compressed by the force of locking the fluid outlet connector to the detecting device and the resilient member imparts a compressing force on the compression spacer.

5. The method in accordance with claim 1 wherein the detecting device includes a fluid inlet connection, and wherein said establishing a flow through the detecting device further comprises:
    introducing a flow of water at the fluid inlet connection;
    adjusting a temperature and a pressure of the water in the detecting device to predetermined values;
    adjusting a dissolved hydrogen concentration and a dissolved oxygen concentration to a predetermined molar ratio; and
    allowing the temperature, pressure, the dissolved hydrogen concentration, and the dissolved oxygen concentration to stabilize for a predetermined period of time.

6. The method in accordance with claim 5 wherein adjusting a temperature and a pressure of the water in the detecting device comprises adjusting the temperature of the flow of water at the inlet connection to a range of about 250 degrees Celsius to about 310 degrees Celsius, and adjusting the pressure within the detecting device to a range of about 900 psig to about 2200 psig.

7. The method in accordance with claim 6 wherein adjusting a temperature and a pressure of the water in the detecting device comprises adjusting the temperature of the flow of water at the inlet connection to a range of about 270 degrees Celsius to about 300 degrees Celsius, and adjusting the pressure within the detecting device to a range of about 950 psig to about 1200 psig.

8. The method in accordance with claim 7 wherein adjusting a temperature and a pressure of the water in the detecting device comprises adjusting the temperature of the flow of water at the inlet connection to about 288 degrees Celsius and the pressure within the detecting device to about 1000 psig.

9. The method in accordance with claim 5 wherein adjusting a dissolved hydrogen concentration and a dissolved oxygen concentration to a predetermined molar ratio comprises adjusting the dissolved hydrogen concentration and the dissolved oxygen concentration molar ratio to greater than about 1.0.

10. The method in accordance with claim 5 wherein adjusting a dissolved hydrogen concentration and a dissolved oxygen concentration to a predetermined molar ratio comprises adjusting the dissolved hydrogen concentration and the dissolved oxygen concentration molar ratio to greater than about 2.0.

11. The method in accordance with claim 1 wherein the detecting array includes a plurality of fluid bores therethrough sized to provide a predetermined pressure drop across the detecting array, the center line of each bore located a different radial distance away from a longitudinal axis of the detecting array than each other bore, and wherein said establishing a flow through the detecting device further comprises:
    establishing a flow through a central bore that includes the longitudinal axis of the detecting array; and
    establishing a flow through each fluid bore adjacent to a corresponding electrode such that the flow exiting the fluid bore flows across the corresponding electrode.

12. The method in accordance with claim 1 wherein measuring an electrical potential comprises measuring an electrical potential to determine the depth of catalyst penetration relative to the oxidant depth of penetration.

13. An apparatus for measuring an electrochemical corrosion potential of a material specimen comprising:
    a holder comprising a first end and a second end, said second end removably coupled to a fluid outlet;
    a detector array comprising a body having a plurality of bores therethrough, said body comprising a detecting face and a second opposing face, said body contained in said holder first end;
    at least one electrode comprising a tip and a wire, said electrode positioned in a portion of said plurality of bores such that an electrode tip extends outwardly from said detecting face and said wire extends from said tip, though said portion of said plurality of bores, and extending from said second face, said tip and wire held frictionally in place within said bore; and
    a fluid inlet coupled to said holder such that fluid entering said inlet flows through a second portion of said plurality of bores from said second face to said detecting face.

14. An apparatus in accordance with claim 13 wherein said holder further comprises:
    a bore therethrough from said first end to said second end;
    a fluid outlet connector removably coupled to said second end;
    a resilient member engaged between said fluid outlet connector and a compression spacer such that a longitudinal compressive force is imparted from said connector through said resilient member to a first face of said compression spacer, said resilient member, fluid outlet connector, and compression spacer co-axially aligned.

15. An apparatus in accordance with claim 13 wherein said detector array further comprises:
    a central bore therethrough about a longitudinal axis of said body, said bore extending from said detecting face to said second face;
    at least one water bore therethrough parallel to said longitudinal axis, said at least one water bore located radially a first distance from said longitudinal axis; and
    an electrode bore corresponding to each said at least one water bore, said electrode bore parallel to said longitudinal axis and located radially a second distance from said longitudinal axis wherein said first distance is larger than said second distance.

16. An apparatus in accordance with claim 15 wherein each said water bore and corresponding electrode bore are located on the same radius line.

17. An apparatus in accordance with claim 15 wherein each of said electrode bores is located a different radial distance from said longitudinal axis than any other electrode bore.

18. An apparatus in accordance with claim 13 wherein said electrode comprises a platinum wire.

19. An-apparatus in accordance with claim 13 wherein said electrode comprises a metal oxide wire.

20. An apparatus for measuring an electrochemical corrosion potential of a material specimen comprising:
    a holder comprising a first end, a second end removably coupled to a fluid outlet, and a resilient member engaged between said fluid outlet and a compression spacer such that a longitudinal compressive force is imparted from said fluid outlet through said resilient member to a first face of said compression spacer, said resilient member, fluid outlet connector, and compression spacer being co-axially aligned;

a detector array comprising a body having a plurality of bores therethrough, said body comprising a detecting face and a second opposing face, said body contained in said holder first end;

at least one platinum wire electrode comprising a tip, said tip comprising an expanded portion and a wire, said electrode positioned in a portion of said plurality of bores such that an electrode tip extends outwardly from said detecting face and said wire extends from said tip, though said portion of said plurality of bores, and extending from said second face, said tip and wire held frictionally in place within said bore; and a fluid inlet coupled to said holder such that fluid entering said inlet flows through a second portion of said plurality of bores from said second face to said detecting face.

* * * * *